_United States Patent_ [19]

Yamauchi et al.

[11] 4,182,035

[45] Jan. 8, 1980

[54] ADHESIVE COMPOSITIONS FOR THE HARD TISSUES OF THE HUMAN BODY

[75] Inventors: Junichi Yamauchi, Kurashiki; Kunitake Yamada, Kagamihara; Kyoichiro Shibatani, Kurashiki, all of Japan

[73] Assignee: Kuraray Company Limited, Kurashiki, Japan

[21] Appl. No.: 829,486

[22] Filed: Aug. 31, 1977

[30] Foreign Application Priority Data

Aug. 31, 1976 [JP] Japan ................. 51-104772

[51] Int. Cl.$^2$ ........................... A61K 5/06
[52] U.S. Cl. ..................... 433/228; 260/42.15; 260/42.53; 260/998.11
[58] Field of Search ............. 260/998.11, 42.15, 42.53; 526/217, 222; 32/15

[56] References Cited

U.S. PATENT DOCUMENTS

| | | | |
|---|---|---|---|
| 2,746,947 | 5/1956 | Kominami et al. | 526/217 |
| 2,758,106 | 8/1956 | Bredereck et al. | 526/217 |
| 2,846,418 | 8/1958 | Brederick et al. | 526/217 |
| 2,987,500 | 6/1961 | Rossetti | 526/222 |
| 3,166,539 | 1/1965 | Schuchardt | 526/217 |
| 3,345,350 | 10/1967 | Shavit et al. | 526/217 |
| 3,740,850 | 6/1973 | Bowen et al. | 32/15 |
| 3,825,518 | 7/1974 | Foster et al. | 260/998.11 |
| 3,926,906 | 12/1975 | Lee et al. | 260/42.15 |
| 4,001,939 | 1/1977 | Gross | 32/15 |

FOREIGN PATENT DOCUMENTS 792812 4/1958 United Kingdom.

_Primary Examiner_—Sandra M. Person
_Attorney, Agent, or Firm_—Oblon, Fisher, Spivak, McClelland & Maier

[57] ABSTRACT

An adhesive composition is provided for the hard tissues of the human body which comprises (1) a radical-polymerizable monomer and a curing system comprising (2) a peroxide, (3) an amine (or its salt) and (4) a salt of a sulfinic acid. The composition is available in two independent packages, one of which contains (1) and (2) the other package (3) and (4). Alternatively, one package contains (1) and (3) the other package (2) and (4).

9 Claims, No Drawings

ADHESIVE COMPOSITIONS FOR THE HARD TISSUES OF THE HUMAN BODY

BACKGROUND OF THE INVENTION

1. Field of the Invention

This invention relates to a curing system for use in adhesive compositions applicable to the hard tissues of the human body, such as teeth and bones. More particularly, the invention relates to a curing system for use in adhesive compositions wherein high adhesion to the hard tissues of the human body are required under wet conditions, said compositions being typically an adhesive for the treatment of a complex fracture of the bone, a filling agent for the fixation of artificial joints, a dental adhesive, a dental filling agent, and the like.

2. Description of the Prior Art

It has been common practice in the field of dental filling to cure a mixture of polymethyl methacrylate powders and methyl methacrylate monomer with a redox curing agent, i.e. a binary system consisting either of a peroxide and an amine or a peroxide and sulfinic acid (or a salt thereof) (BP No. 1,130,653). It is also known to cure a mixture of bisphenol-A diglycidyl methacrylate and triethylene glycol dimethacrylate in the presence of an inorganic filler using a binary redox curing system consisting either of a peroxide and an amine or a peroxide and sulfinic acid (U.S. Pat. No. 3,926,906). However, when a two-component redox curing agent of the peroxide-amine type is employed, the polymerizate exhibits substantially no adhesion to the hard tissues of human body, the bond strength under wet conditions being only on the order of 0 to 5 kg/cm$^2$. Therefore, in dental practice, to make up for such deficiency in adhesion, mechanical-retaining means known as an undercut is provided in the tooth cavity so as to prevent displacement of the filling material after curing. This practice, however, has the disadvantage that the healthy tissue of the tooth is also removed. Because of the lack of bonding between the filling material and the tooth, this procedure provides only a poor marginal seal, which tends to cause a recurrence of the decay. The use of a two-component redox curing system consisting of a peroxide and sulfinic acid has been found not to be practical because of the extreme instability of sulfinic acid. Although this instability can be overcome by converting sulfinic acid to an amine salt thereof (BP No. 653,597), it has been found that such conversion to a salt causes a significant reduction in the rate of curing. Therefore, despite the knowledge that sulfinic acid and its salts can be components of curing systems for dental filling materials, to the best of our knowledge it has been, at best little used in practice. It is known that the degree of adhesion to the hard tissues of human bodies can be varied by using various components for the curing system. For example, the use of trialkylborane as a curing agent is known (Japanese Pat. Publ. No. 14318/1967). While this curing agent displays high adhesion to the dentin of the tooth, it has only poor adhesion to the enamel of the tooth, which contains little organic matter. Moreover, trialkylborane is not easy to handle for it is an unstable compound which, for instance, tends to ignite in air. It is also known that, in an organic peroxide-amine (or-sulfur compound) system, the addition of a hydroperoxide in a small amount is beneficial (U.S. Pat. No. 4,001,939). However, it does not possess adequate adhesion to the tooth and equivalent tissues. Thus, the current status of the art, no agent has been discovered that displays adequate adhesion to hard human tissues which is practical.

To obtain a satisfactory adhesion to the hard tissues of the human body, it is known to admix a monomer such as methyl methacrylate or bisphenol-A diglycidyl methacrylate with a small amount of a phosphoric acid ester monomer and cure the mixture (Journal Dental Research 35, p. 846, U.S. Pat. No. 3,882,600). According to the Journal Dental Research, dimethacryloxyglycerophosphoric acid is added to methyl methacrylate and the mixture is cured with a curing system consisting of benzoyl peroxide and p-toluenesulfinic acid. However, as discussed previously, p-toluenesulfinic acid is unstable and, moreover, the bond strength obtainable is low, 15 to 30 kg/cm$^2$. U.S. Pat. No. 3,882,600 teaches a method which comprises adding glycerol dimethacrylate monofluorophosphate to a phthalate monomer and curing the mixture with a curing system consisting of benzoyl peroxide, N,N-dimethyl-3,5-dimethylaniline and dodecyl mercaptan. This curing system, however, tends to give off an odor which is objectionable in oral use and the monomer system employed has a physiologically injurious effect presumably due to the P-F bond.

A ternary curing system consisting of sulfinic acid, atmospheric oxygen (or dibenzoyl peroxide) and dimethylaniline is known to be an effective catalyst in the polymerization of methyl methacrylate or vinyl acetate (Bulletin Journal Chemical Society of Japan 32, 1079 (1959), Kobunshi Kagaku, Vol. 10, p. 441). However, this literature contains no reference to salts of sulfinic acid, nor does it even suggest the application of such a ternary system to an adhesive composition for the hard tissues of human bodies.

Among the properties required of such curing agents, there may be mentioned sufficient shelf life and an instant curing activity such that when used by a dentist or surgeon, it cures the monomer at room temperature without undue delay. It has found that, to meet the two requirements, the two components of a curing system, i.e. peroxide and amine (or sulfinic acid), are separately packaged and, when the system is used, the two packages are admixed (U.S. Pat. No. 3,926,906). However, this technique is not satisfactory when sulfinic acid is employed.

Other literature may also be cited as evidence that sulfinic acid (or its salt) is useful as a polymerization initiator. For example, German Pat. No. 1,138,226 and No. 1,123,824 describe the use of sulfinic acid in combination with a quaternary ammonium salt, or of a salt of sulfinic acid in conjunction with a quaternary ammonium salt. However, when put to use, these systems are by no means practical because of the low curing rates obtained.

SUMMARY OF THE INVENTION

It is, therefore, an object of this invention to provide an adhesive composition for the hard tissues of the human body which displays firm, sustained stable adhesion to bones and to dentin and enamel of teeth and which, when applied to the human body, exhibits a high cure rate to give a colorless cross-linked polymerizate.

It is another object of this invention to provide an adhesive composition for the hard tissues of the human body which is of value as a dental filling material.

It is still another object of this invention to provide an adhesive composition which is of value as a adhesive agent for bonding dental filling material to teeth.

Other objects of this invention will become apparent from the following detailed description.

The above objects are accomplished by using an adhesive composition comprising a free radical-polymerizable monomer and a curing system comprising a peroxide, an amine (or a salt thereof) and a salt of a sulfinic acid compound.

DETAILED DESCRIPTION OF THE PREFERRED EMBODIMENTS

As the free radical-polymerizable monomer to be employed in this invention, use may be made of any monomer of the type that is liquid and not especially harmful to the human body. Thus, acrylic (or methacrylic) acid esters, vinyl acetate, styrene, etc. may be mentioned. Particularly desirable are the acrylic (or methacrylic) acid ester derivatives. Thus, methyl acrylate (or methacrylate), ethyl acrylate (or methacrylate), hydroxyethyl acrylate (or methacrylate), bisphenol-A dimethacrylate (diacrylate), 2,2'-bis(acryloxy(or methacryloxy)ethoxyphenyl) propane, 2,2'-bis($\gamma$-acryloxy(or methacryloxy)-$\beta$-hydroxypropoxyphenyl) propane, neopentyl glycol diacrylate (or dimethacrylate), mono-, di-, tri- or tetra-ethylene glycol diacrylate (or dimethacrylate), etc. may be mentioned. Particularly, 2,2'-bis($\gamma$-methacryloxy-$\beta$-hydroxypropoxyphenyl) propane (BIS-GMA) is employed as a principal component in many compositions. Such monomers are employed alone or as a mixture. In addition to the above-mentioned monomers, the monomers mentioned in Japanese Patent Application No. 98878/1974 which corresponds to U.S. Pat. No. 3,872,047) may also be employed. Particularly, carboxyl-containing monomers such as acrylic acid, methacrylic acid, maleic anhydride, crotonic acid, etc.; nitrogen-containing monomers such as vinylpyridine, vinylpyrrolidone, vinylcarbazole, etc.; sulfo-containing monomers such as vinylsulfonic acid, 2-sulfoethyl methacrylate, etc.; and monomers containing phosphoric acid groups such as glycerinphosphoric acid, methacryloxyethyl phosphate, glycerol dimethacrylate monofluorophosphate, etc. may be employed alone or in combination with the known acrylic (or methacrylic) acid ester monomers.

The peroxide used as a component of the curing system of this invention can be any peroxide that is generally used as a curing component. Preferred are diacyl peroxides such as dibenzoyl peroxide, di-p-chlorobenzoyl peroxide, dilauroyl peroxide, etc. Especially desirable is dibenzoyl peroxide.

The amine employed according to this invention is desirably a compound such that an amino group is attached to an aryl group and, preferably, a secondary or tertiary amine rather than a primary amine, for the use of a secondary or tertiary amine leads to significantly accelerated curing.* As the preferred amines may be mentioned N,N-dimethylaniline, N,N-dimethyl-p-toluidine, N-methyl-N-$\beta$-hydroxyethylaniline, N,N-di($\beta$-hydroxyethyl) aniline, N,N-di($\beta$-hydroxyethyl)-p-toluidine, N-methylaniline, N-methyl-p-toluidine, etc. These amine compounds may be salts such as the hydrochlorides, acetates and phosphates.

*The aryl group is more preferably benzene or naphthalene derivatives of carbon numbers 6 to 30.

The salt of sulfinic acid employed in this invention may be a salt of any organic sulfinic acid but in terms of stability, a salt of a sulfinic acid attached to an aryl group is desirable.** The salts may be alkali metal salts, alkaline earth metal salts and amine salts, although alkali and alkaline earth metal salts are preferred to amine salts in terms of stability. As examples of the salt of sulfinic acid, there may be mentioned sodium benzenesulfinate, calcium benzenesulfinate, strontium benzenesulfinate, ammonium benzenesulfinate, triethyl ammonium benzenesulfinate, benzenesulfinic acid N,N-dimethyl-p-toluidine salt, and various salts of p-toluenesulfinic acid, $\beta$-naphthalenesulfinic acid, styrenesulfinic acid, etc. Particularly desirable are salts of benzenesulfinic acid.

*The aryl group is more preferably benzene or naphthalene derivatives of carbon numbers 6 to 30.

As mentioned previously, the curing system of this invention consists essentially of the above-mentioned three components, namely a peroxide, an amine (or a salt thereof) and a salt of sulfinic acid. It has been surprisingly discovered that the use of these three components results in a significant improvement in adhesion to the hard tissues of human body. Such effects have never been accomplished by the conventional binary peroxide-amine systems. It remains yet to be fully elucidated why such effects come into being but it is likely that the salt of sulfinic acid has an extraordinary affinity for the hard tissues of human bodies and, as it consitutes a curing composition in conjunction with a peroxide-amine system, the salt is responsible for a special interaction between the polymerizate and such tissues. It has also been found that compared with the conventional peroxide-sulfinic acid system or peroxide-sulfinic acid-amine system, the ternary curing system of this invention brings about a significant improvement in stability. It has further been found that the acid monomers, such as carboxyl containing monomers, sulfo-containing monomers, and monomers containing phosphoric acid group, can be rapidly polymerized alone or in combination with the known acrylic (methacrylic) acid ester monomers, with the ternary curing system of this invention. Such effects have also never been accomplished by the conventional binary peroxide-amine systems. Based on the free radical-polymerizable monomer, the curing composition is employed within the range of 1 to 20 weight percent, the relative amount being selected to ensure that the curing time will be no more than 10 minutes. As to the preferred proportions of the individual constituents of the curing system, that of peroxide is within the range of 0.1 to 5 weight percent, inclusive (more preferably 0.5 to 3%, inclusive), that of amine (or its salt) is 0.1 to 5 weight percent, inclusive (more preferably 0.5 to 3%) and that of sulfinic acid salt is 1 to 10 weight percent, inclusive (more preferably 2 to 6%), all based on the polymerizable monomer. Particularly, the amount of the sulfinic acid salt is preferably large to improve adhesion to the hard tissues of human body, but it is desirably within the above range because of the possibility of increased extraction or elution from the polymerizate.

As necessary, other polymers, fillers, stabilizers and so forth may be incorporated in the composition of this invention. As the polymers incorporated to reduce the polymerization shrinkage or for viscosity adjustment, there may be mentioned polymethyl acrylate (or methacrylate), polyethyl acrylate (methacrylate), polyhydroxyethyl methacrylate, polystyrene, unsaturated polyesters, etc. The fillers may be glass beads, aluminum oxide, $\alpha$-quartz powders, colloidal silica, etc. within the range of about 1 to 100$\mu$ in particle diameter.

As examples of said stabilizers, there may be mentioned hydroquinone monomethyl ether, t-butyl-p-cresol, hydroxymethoxybenzophenone, etc.

Although it is stated in BP No. 753,597 that, where sulfinic acid is employed, the presence of a low molecular weight inorganic acid is essential, the presence of such an inorganic acid is not necessary for the composition of this invention.

In practice, the doctor, dentist or other qualified person prepares the adhesive composition of this invention and applies it to the hard tissue of his patient, whereupon the composition cures inside the hard tissue or in contact with the tissue. Normally, in order to save on the effort of the doctor, for instance, the composition is previously prepared within the limits where its stability can be assured, and supplied to him in packages. U.S. Pat. No. 3,926,906 teaches a two-package form containing a peroxide and an amine (or sulfinic acid) in independent packages, with a mixture of the monomer and inorganic filler being contained in each package so as to ensure a shelf life of the adhesive composition and, at the same time, to facilitate the practice of the doctor or dentist. However, it has been found that the system according to this invention tends to decompose or degrade the monomers, particularly methacrylic (and acrylic) derivatives when stored together. Based on this finding, we further found that the following package forms are practically advantageous.

[1] The peroxide is dissolved in the polymerizable monomer and the mixture is packaged. Package A. On the other hand, the amine (3) is admixed with the sulfinic acid salt (4) and the mixture is packaged. Package B.

[2] The amine (3) is previously dissolved in the polymerizable monomer (1) and the mixture is packaged. Package (A'). The peroxide (2), e.g. benzoyl peroxide powders, and the sulfinic acid salt (4) are packaged together. Package (B').

Preferably, an inorganic or polymer filler powder is incorporated in Package (B) or (B') to dilute the curing components. In another preferred practice, the components in Package (B) or (B') is dissolved and diluted with a volatile organic solvent. As the case may be, the components in Package (B) or (B') is preferably formed in a pasty state, diluted with a volatile solvent and colloidal silica. Said inorganic or polymer powder may be selected from the known materials mentioned previously. The volatile organic solvent may be any solvent which is low-boiling (150° C. or less) and least irritating to the dental pulp thus being exemplified by alcohols, e.g. methanol, ethanol and butanol; ethers, e.g. ethyl ether; ketones, e.g. acetone; and esters such as methyl acetate. Particularly preferred are alcohols, for they dissolve the curing components. Of the above-mentioned two-package forms, the package form [1] is preferred to the package form [2] in terms of stability, for in the latter, the sulfinic acid salt and peroxide tend to undergo degradation at high temperatures even though they are admixed as powders. The above two-package forms are stable over an extended time, this being particularly true of the package form [1]. Moreover, merely by admixing the contents of the two packages, the doctor or dentist may easily obtain the adhesive composition of this invention.

The application of the adhesive composition to the hard tissue may be accomplished in the following manner. The adhesive composition is mixed into a filling material and the mixture is allowed to cure in situ, whereby an improved bond is established between the filling material and the hard tissue. Alternatively, the adhesive composition is coated over the surface of the affected tooth or bone as a liner and, then, the conventional filling material is applied. The composition is now allowed to cure, whereby an improved bond is obtained between the filling agent and the hard tissue of the patient. The adhesive composition of this invention may also be employed as an adhesive for inlays, crowns, etc. Because of the particularly significant advantage of the adhesive composition of this invention as it is used as a lining material, this mode of embodiment will now be described in further detail.

A paste composed of polymerizable monomer, polymerization inhibitor, ultraviolet absorber and filler is divided into two equal portions. The peroxide is added to one of the portions, while the amine is added to the other portion. The two paste portions are independently packaged. The sulfinic acid salt and amine are dissolved in a volatile solvent and, separately, the peroxide is dissolved in the polymerizable monomer. Thus, two liquid packaged products are prepared. In use, the two liquid products are admixed to obtain an adhesive primer, which is applied to the part of the hard tissue which needs the treatment. Then, the pastes from the two paste packages are admixed and filled into the primed art. In this manner, an intimate bond is established between the filling material and the hard tissues of human bodies.

It is surprising to observe that by polymerizing the free radical-polymerizable monomer with a ternary curing system according to this invention, a strong bond to the hard tissue of a human body is accomplished under wet conditions, with the bond strength being as high as 100 kg/cm$^2$. It is also surprising that, with the curing system of this invention the disadvantage of the prior art product that the curing reaction proceeds slowly over the surface exposed to air is largely overcome and the discoloration of the cured product is also substantially absent. It has also been found that the admixed adhesive composition of this invention features a comparatively long inhibition period followed by rapid curing. Therefore, when applied to the dental filling and adhesive materials, the adhesive composition of this invention not only offers a considerable procedural advantage but prevents dislocation and displacement of the filling material. Moreover, by keeping the curing system in specified package forms as mentioned hereinbefore until it is put to use, it may enjoy a long shelf life.

Having generally described the invention, a more complete understanding can be obtained by reference to certain specific examples, which are included for purposes of illustration only and are not intended to be limiting unless otherwise specified.

EXAMPLE 1

The components of curing system were admixed by dissolution or dispersion with a liquid monomer (Agent B) consisting of 80 weight parts of methyl methacrylate and 20 weight parts of ethylene glycol dimethacrylate and a poly (methyl methacrylate) powder (Agent A) as indicated in Table 1.

The tertiary amine used was N,N'-di(β-hydroxyethyl)-p-toluidine; the sulfinic acid was p-toluenesulfinic acid; the sulfinic acid salt was sodium p-toluenesulfinate; and the quaternary ammonium compound was benzyltriethylammonium chloride.

The resultant components (A) and (B) were admixed in a ratio of 1 to 1 (by weight) and allowed to cure at room temperature. The cure time, the degree of coloration of the cured product and the surface cure-inhibition were investigated. To measure the wet bond strength with respect to a bar of ivory, the pasty mixture was sandwiched between a wet bar of ivory and a bar of acrylic resin, each having a cross-sectional area of 10 millimeters square and the two bars were placed in abutment. After curing, the assembly was immersed in water at 37° C. for one day. The bond strength was then measured by pulling the bars apart from each other. The results are set forth in Table 1.

The bond strength test was carried out with an Instron Model TT-B tester at a pulling speed of 2 mm/min.

Table 2

| No. of days, immersion in water | 1 | 7 | 20 |
|---|---|---|---|
| Bond strength (Kg/cm$^2$) | 70 | 66 | 67 |

EXAMPLE 3

Components A and B were prepared as follows.

Table 1

| No. | Components and proportions by weight of the curing system (based on monomer) A(polymer powders) | B(liquid monomer) | Cure time (min.) | Coloration of cured product | Surface cure inhibition | Bond strength with respect to ivory bar (kg/cm$^2$) |
|---|---|---|---|---|---|---|
| 1 | Benzoyl peroxide 2% | Tertiary amine 1% | 6 | Colored | Inhibited | 0–2 |
| 2 | Sulfinate 3% | Quaternary ammonium 1% | 16 | Not Colored | Inhibited | 58 |
| 3 | Sulfinic acid 3% | Quaternary ammonium 1% | >10$^4$ | — | — | — |
| 4 | Sulfinate 3% | Tertiary amine 1% | >10$^4$ | — | — | — |
| 5 | Sulfinic acid 3% | Tertiary amine 1% | 7 | Colored | Inhibited | 11 |
| 6 | Sulfinate 3% | — | >10$^4$ | — | — | — |
| 7 | Sulfinate 3% Benzoyl peroxide 2% | Tertiary amine 1% | 4 | Not Colored | Not Inhibited | 80 |
| 8 | Sulfinate 3% Tertiary amine 1% | Benzoyl peroxide 2% | 4 | Not Colored | Not Inhibited | 80 |
| 9 | Sulfinic acid 3% | Benzoyl peroxide 2% | 15 | Not Colored | Inhibited | 54 |
| 10 | Sulfinate 3% | Benzoyl peroxide 2% | >10$^4$ | — | — | — |
| 11* | Sulfinic acid 3% Tertiary amine 1% | Benzoyl peroxide 2% | 4 | Colored | Not Inhibited | 43 |
| 12 | Sulfinic acid 3% | — | 25 | Not Colored | Inhibited | 54 |

*Component A in test Run No. 11 was prepared in two distinct portions, one of which contained sulfinic acid with the other containing the tertiary amine. The two portions were admixed together at the time of conducting the test.

It will be apparent from Table 1 that the benzoyl peroxide-tertiary amine-sodium sulfinate system according to this invention displayed a significantly enhanced adhesion to the bar of ivory, with improved surface cure behavior and a reduced tendency to coloration after curing. In contrast, all the known systems tested produced unsatisfactory results.

EXAMPLE 2

A monomeric mixture of 30 weight parts of bisphenol A-diglycidyl dimethacrylate, 20 weight parts of ethylene glycol dimethacrylate and 50 weight parts of methyl methacrylate was divided in two portions. To one of the portions was added 5 weight parts of ammonium p-toluenesulfinate and 1 weight part of N,N-di(β-hydroxyethyl)-p-toluidine, while 2 weight parts of BPO (benzoyl peroxide) was added to the other portion. Equal portions of these two compositions were taken and admixed immediately after preparing the above compositions, whereby a cured product was obtained in about 5 minutes. The above compositions just prepared were mixed and sandwiched between wet bars of ivory and allowed to cure. This procedure established a firm bond between the bars. Table 2 shows the bond strengths after immersion in water at 37° C. for various times ranging from 1 to 20 days.

| Component A: | |
|---|---|
| Bisphenol-A diglycidyl dimethacrylate | 18.7wt. parts |
| Triethylene glycol dimethacrylate | 3.3wt. parts |
| Silanated α-quartz powders | 77.6wt. parts |
| Benzoyl peroxide | 0.3wt. part |
| Hydroquinone monomethyl ether | 0.1wt. part |
| Component B: | |
| Bisphenol-A diglycidyl dimethacrylate | 18.7wt. parts |
| Triethylene glycol dimethacrylate | 3.3wt. parts |
| Silanated α-quartz powders | 77.2wt. parts |
| Sodium p-Toluenesulfinate | 0.5wt. part |
| N,N'-diethanol-p-toluidine | 0.2wt. part |
| Hydroquinone monomethyl ether | 0.1wt. part |

The silanation of quartz powders was effected by adding 2 weight parts of α-quartz powders to 1 weight part of a aqueous solution containing 1.0% γ-methacryloxypropyltrimethoxysilane and 0.1% acetic acid and, after drying in air streams, the mixture was heat-treated at 100° C. for 30 minutes.

Immediately following the preparation, equal portions of the pasty components A and B were taken and kneaded well, whereby a cured product was obtained in 35 minutes.

The bond strength of the mixed paste with respect to ivory bars was determined under the conditions set forth in Example 2. The strength was found to be 56 kg/cm$^2$ after a day's immersion in water. Using an extracted healthy human front tooth, a cavity 3 mm in diameter and 2 mm deep was formed in the labial a surface thereof by means of an air turbine and, then, the enamel was etched with a 60% aqueous solution of phosphoric acid, rinsed well with water and air-dried. Thereafter, a paste made up of equal portions of components A and B was kneaded and filled into the cavity. The tooth was alternately immersed in aqueous solutions of fuchsin at 0° and 60° C., respectively, for one minute each for a total of 60 times to evaluate the marginal sealing effect. The result indicated substantially no immigration of the dyestuff.

EXAMPLE 4

A dental repairing agent was prepared by employing the adhesive components (A and B) of this invention in combination with the conventional composite resin (C, D) and etching agent (E). Each of the components had the following composition.

| | |
|---|---|
| Component A: | |
| 2,2'-bis[p-($\gamma$-Methacryloxy-$\beta$-hydroxypropoxy) phenyl] propane(Bis-GMA) | 30.00wt. parts |
| Neopentyl glycol dimethacrylate | 60.00wt. parts |
| 2 - Hydroxyethyl methacrylate | 10.00wt. parts |
| Dibenzoyl peroxide | 2.00wt. parts |
| Hydroquinone monomethyl ether | 0.03wt. part |
| 2-Hydroxy-4-methoxybenzophenone | 0.03wt. part |
| 2,6-di-t-butyl-p-cresol | 0.02wt. part |
| Component B: | |
| Ethyl alcohol | 93.00wt. parts |
| Sodium benzenesulfinate | 6.00wt. parts |
| N,N-diethanol-p-toluidine | 1.50wt. parts |
| Hydroquinone monomethyl ether | 0.03wt. part |
| 2-Hydroxy-4-methoxybenzophenone | 0.03wt. part |
| 2,6-di-t-Butyl-p-cresol | 0.02wt. part |
| Component C: | |
| Quartz powders | 75.00wt. parts |
| Triethylene glycol dimethacrylate | 8.00wt. parts |
| 2,2'-bis[p-($\gamma$-Methacryloxy-$\beta$-hydroxypropoxy) phenyl] propane (Bis-GMA) | 15.00wt. parts |
| Colloidal silica | 2.00wt. parts |
| Dibenzoyl peroxide | 0.50wt. part |
| Hydroquinone monomethyl ether | 0.01wt. part |
| 2,6-di-t-Butyl-p-cresol | 0.01wt. part |
| 2-Hydroxy-4-methoxybenzophenone | 0.01wt. part |
| Component D: | |
| Quartz powders | 75.00wt. parts |
| Triethylene glycol dimetharylate | 8.00wt. parts |
| 2,2'-bis [p-($\gamma$-Methacryloxy-$\beta$-hydroxypropoxy) phenyl] propane (Bis-GMA) | 15.0wt. parts |
| Colloidal silica | 2.00wt. parts |
| N,N-diethanol-p-toluidine | 0.20wt. part |
| Hydroquinone monomethyl ether | 0.01wt. part |
| 2-Hydroxy-4-methoxybenzophenone | 0.01wt. part |
| 2,6-di-t-Butyl-p-cresol | 0.01wt. part |
| Dye | Trace |
| Component E: | |
| Orthophosphoric acid | 60.00wt. parts |
| Water | 40.00wt. parts |
| Collodial silica | 2.00wt. parts |
| Dye | Trace |

Components A and B are the dentin-adhesive primer containing the curing system according to this invention and can be stored without degradation over a period of more than one year at room temperature. When A and B are admixed together in equal parts, the mixture cures in several minutes. Components C and D together provide a cured product resembling the human tooth in hardness, strength and color and can be stored over a period of more than one year. If equal parts of C and D are admixed together, a cured product is obtained in several minutes. The component E is an etching agent for the enamel of the human tooth and assists in the bonding of the adhesive agent to the enamel.

By means of an air turbine, a cavity was formed in an extracted healthy human tooth (about 2 mm deep; widths: about 6 mm, max. and about 3 mm, min.). The agent E was coated on the wall and marginal area of the cavity and, after one minute, rinsed with water and dried by means of compressed air. Then, one drop each of components A and B was taken on a duppen glass and, after admixing, the mixture was coated on the bottom, side wall and vicinity of the cavity. The area coated with the adhesive was exposed to compressed air, whereby the ethanol was evaporated off. Equal parts of C and D were taken and kneaded together and the mixture was filled into the cavity. After curing, the repaired material was buffed and finished with a diamond burr. The above procedure resulted in a repair which was as attractive and hard as the natural tooth.

In a percolation test which comprised dipping the repaired tooth alternately in aqueous solutions of fuchsin at 0° C. and 60° C., respectively, for one minute each for a total of 60 times, the repaired tooth, as above, showed no evidence of the dye between the repairing material and the tooth, thus demonstrating the excellent bonding result.

EXAMPLE 5

A dental repairing material was prepared by employing the adhesive components (A and B) in combination with conventional composite resins (C and D) and etching agent (E). Each components had the following composition.

| | |
|---|---|
| Component A (powder) | |
| Silanated quartz powders (250 mesh pass) | 100.00wt. parts |
| N,N-diethanol-p-toluidine | 1.50wt. parts |
| Sodium benzenesulfinate | 5.00wt. parts |
| Component B (liquid): | |
| 2-Hydroxyethyl methacrylate | 45.00wt. parts |
| 2,2'-bis[p-($\gamma$-Methacryloxy-$\beta$-hydroxypropoxy) phenyl] propane (Bis-GMA) | 35.00wt. parts |
| Neopentyl glycol dimethacrylate | 20.00wt. parts |
| Dibenzoyl peroxide | 1.00wt. part |
| Hydroquinone monomethyl ether | 0.03wt. part |
| Component C: | |
| The same as Component C of Example 4 | |
| Component D: | |
| The same as Component D of Example 4 | |
| Component E: | |
| The same as Component E of Example 4 | |

When A and B are mixed together in equal proportions, curing takes place in a few minutes. However, Components A and B as kept separate from each other remain stable at room temperature over a period of more than one year. At an elevated temperature of 35° C., no degradation was in evidence for 2 months.

In an extracted healthy human tooth, there was formed a cavity similar to that described in Example 4. First, Component E was applied as in Example 4. The cavity was rinsed with water and dried. Equal parts of Components A an B were taken and mixed on a Duppen glass and, with a small brush, the mixture was coated on the bottom and side walls and the vicinity of the cavity. Then, equal parts of Components C and D were kneaded together and the mixture was filled into the cavity. The repaired tooth was finished as in Example 4. In a percolation test similar to that described in Example 4, there was no evidence of dye infiltration between the repairing material and the tooth.

As a control, sodium benzenesulfinate was omitted from Component A to prepare Component A' and the repairing of a tooth was performed using Component A' and B in otherwise the same manner. The mixture of equal parts of A' and B cured 1 to 2 minutes later than the mixture of A and B. The components E, C and D were applied precisely in the same manner as described above. However, with the adhesive agent of A' and B, a percolation test showed an infiltration of dye to the cavity bottom. The above results of test runs demonstrate the extraordinary effect of the catalyst system of this invention.

EXAMPLE 6

A liquid component X was prepared using 60 weight parts of methyl methacrylate, 20 weight parts of 2-hydroxyethyl methacrylate, 20 weight parts of ethylene glycol dimethacrylate, 1.6 weight parts of dibenzoyl peroxide, 0.02 weight part of 2,6-di-t-butyl p-cresol and 0.03 weight part of 2-hydroxy-4-methoxybenzophenone. A powder component Y was prepared by adding 1.0 weight part of N,N-diethanol-p-toluidine and a varying amount (Table 2) of sodium benzenesulfinate to 100 weight parts of finely divided polymethyl methacrylate (mol. wt. 130,000; 250 mesh approx.). The two components X and Y were admixed in a weight ratio of 1:1 and the mixture was applied to the 10 mm × 10 mm faces of two wet bars of ivory each measuring 10 mm × 10 mm × 100 mm. The coated faces were placed in abutment and the coating was allowed to cure at room temperature. After curing, the assembly was immersed in water at 37° C. for 72 hours, after which the bars were pulled apart on an Instron Model TT-B tester at a pulling rate of 2 mm/min. to determine the bond strength. The cure time and bond strength data are given in Table 2. Each bond strength value shown is the average of the results of 8 Instron test runs.

Table 2

| Sample No. | Sodium benzenesulfinate (wt % in Y) | Cure time (min.) at room temp. | Bond strength (kg/cm$^2$) |
|---|---|---|---|
| 1 | 0 | 10 | 1.8 |
| 2 | 1 | 9 | 29 |
| 3 | 2 | 8 | 56 |
| 4 | 4 | 5 | 84 |
| 5 | 10 | 3 | 142 |

With an increased proportion of sodium benzenesulfinate, there was a steep gain in bond strength and a reduction in cure time. It should be noted, however, that the addition of an excessively large amount of sodium benzenesulfinate would be undesirable, for it should lead to an increased extraction of the salt from the cured material.

In a separate experiment, it has been found that whereas an increased amount of N,N-diethanol-p-toluidine leads to a reduced cure time, an increased amount of benzoyl peroxide does not yield such a result and that an increased amount of N,N-diethanol-p-toluidine or-/and of benzoyl peroxide does not contribute to a greater bond strength. It was rather surprising to discover that bond strengths depend solely upon the amount of sodium sulfinate employed. Moreover, bond strengths remained essentially unchanged when the cured products were allowed to stand in water at 37° C. for 90 days or at 60° C. for 60 days. Component X and, irrespective of the amount of sodium benzenesulfinate. Component Y were both found to be stable when kept in an oven at 37° C. for no less than two months, thus suggesting that both components have excellent shelf lives.

Further, 1.6 weight parts of dibenzoyl peroxide was replaced with 1.0 weight part of N,N-diethanol-p-toluidine in Component X to prepare a liquid Component X'. On the other hand, 1.0 weight part of N,N-diethanol-p-toluidine was replaced with 1.6 weight parts of dibenzoyl peroxide to prepare a powdery Component Y' (The sodium benzenesulfinate in Table 2 was contained herein). Whereas the use of X' and Y' immediately after preparation produced the curing characteristics and dentin-adhesive properties comparable to those of the combination of X and Y, the former combination X' and Y' showed a tendency toward a slightly increased cure time when they had been kept in an oven at 37° C. for 2 months. In terms of shelf life, it is apparently more advantageous that the sulfinic acid salt be packaged together with the amine component than with dibenzoyl peroxide.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A packaged adhesive composition for bonding a dental filling material to the tooth, comprising two independent packages, the content of which may be admixed in use wherein said adhesive composition comprises a radical-polymerizable monomer (1), a diacyl peroxide (2), a secondary or tertiary amine attached to an aryl group (3) and an alkali or alkaline earth metal salt of an arylsulfinic acid (4), wherein one of said packages contains components (1) and (2), while the other package contains components (3) and (4), which are dissolved in a volatile solvent.

2. The packaged adhesive composition of claim 1, wherein said radical-polymerizable monomer is an acrylic or methacrylic acid ester derivative.

3. The packaged adhesive composition of claim 1, wherein said peroxide is dibenzoyl peroxide.

4. The packaged adhesive composition of claim 1, wherein said amine is N,N'-di(β-hydroxyethyl)-p-toluidine.

5. The packaged adhesive composition of claim 1, wherein said alkali or alkaline earth metal salt of an arylsulfinic acid is sodium benzenesulfinate, calcium benzenesulfinate or strontium benzenesulfinate.

6. The packaged adhesive composition of claim 1, wherein said diacyl peroxide is present in an amount of 0.5 to 3 weight percent based on a radical-polymerizable monomer, said secondary or tertiary amine in an amount of 0.5 to 3 weight percent and said sulfinic acid salt in an amount of 2 to 6 weight percent on the same basis.

7. The packaged adhesive composition of claim 1, wherein said volatile solvent is ethanol.

8. A dental restoration material comprising a dental filling composition and a dental adhesive composition for bonding said filling composition to the tooth, which comprises two independent packages, the content of which may be admixed in use wherein said adhesive composition comprises a radical-polymerizable monomer (1), a diacyl peroxide (2), a secondary or tertiary amine attached to an aryl group (3) and an alkali or alkaline earth metal salt of an arylsulfinic acid (4), wherein one of said packages contains components (1) and (2), while the other package contains components (3) and (4), which are dissolved in a volatile solvent.

9. A method for filling a tooth cavity including the step of (i) preparing a lining composition by admixing two independent packages, one of which contains a radical-polymerizable monomer and a diacyl peroxide, while the other contains a secondary or tertiary amine attached to an aryl group and an alkali or alkaline earth metal salt of an arylsulfinic acid, which are dissolved in a volatile solvent, (ii) applying said lining composition to the walls of the tooth cavity, (iii) drying around the area coated with the said lining composition to evaporate a volatile solvent and then (iv) filling the remainder of the cavity with a dental filling material.

* * * * *

UNITED STATES PATENT AND TRADEMARK OFFICE
CERTIFICATE OF CORRECTION

PATENT NO. : 4,182,035
DATED : January 8, 1980
INVENTOR(S) : Junichi Yamauchi et al It is certified that error appears in the above—identified patent and that said Letters Patent is hereby corrected as shown below:

Column 1, line 48, delete "653,597" and insert --753,597

Column 8, line 64, delete "35", insert --3--

Signed and Sealed this

Thirteenth Day of January 1981

[SEAL]

Attest:

SIDNEY A. DIAMOND

Attesting Officer    Commissioner of Patents and Trademarks